United States Patent [19]
Katsumata et al.

[11] Patent Number: 5,521,074
[45] Date of Patent: May 28, 1996

[54] PROCESS FOR PRODUCING L-VALINE

[75] Inventors: Ryoichi Katsumata; Shinichi Hashimoto, both of Machida, Japan

[73] Assignee: Kyowa Hakko Kogyo Co., Ltd., Japan

[21] Appl. No.: 450,079

[22] Filed: May 25, 1995

Related U.S. Application Data

[63] Continuation of Ser. No. 313,945, Sep. 28, 1994, abandoned, which is a continuation of Ser. No. 172,671, Dec. 22, 1993, abandoned, which is a continuation of Ser. No. 955,536, Oct. 1, 1992, abandoned, which is a continuation of Ser. No. 760,559, Sep. 16, 1991, abandoned.

[30] Foreign Application Priority Data

Sep. 18, 1990 [JP] Japan ................................ 2-248550

[51] Int. Cl.$^6$ ............................... C12P 13/08; C12N 1/20
[52] U.S. Cl. ..................... 435/115; 435/106; 435/252.1; 435/252.32; 435/840; 435/843
[58] Field of Search ...................... 435/106, 115, 435/252.1, 252.32, 840, 843

[56] References Cited

PUBLICATIONS

Abstract J6–3160–592–A, Jul. 1988.
Abstract JA–027738 of DT2411209, Sep. 1974.
Abstract JA–031812 J51106788, Sep. 1976.

*Primary Examiner*—Herbert J. Lilling
*Attorney, Agent, or Firm*—Pennie & Edmonds

[57] ABSTRACT

There is provided a process for producing L-valine which comprises cultivating, in a medium, a microorganism which belongs to the genus Corynebacterium or Brevibacterium, which exhibits a) an ability to produce L-valine, b) resistance to L-valine in a medium containing acetic acid as a sole carbon source, and c) sensitivity to a pyruvic acid analog in a medium containing glucose as a sole carbon source, until L-valine is accumulated in the culture broth, and recovering L-valine therefrom.

1 Claim, No Drawings

PROCESS FOR PRODUCING L-VALINE

This is a continuation of application Ser. No. 08/313945, filed Sep. 28, 1994, now abandoned, which is a continuation of application Ser. No. 08/172,671, filed Dec. 22, 1993, now abandoned, which is a continuation of application Ser. No. 07/955,536, filed Oct. 1, 1992, now abandoned, which is a continuation of U.S. Ser. No. 07/760,559 filed on Sep. 16, 1991, now abandoned.

BACKGROUND OF THE INVENTION

The present invention relates to a process for producing L-valine. L-valine is an amino acid which is mainly used as a medicament such as nutrient infusion and amino acid complex preparations and is also used as seasonings and animal feed.

Various processes for producing L-valine Coryneform glutamic acid-producing bacteria that belongs to the genus Corynebacterium or Brevibacterium have been known; for example, a process using microorganisms having resistance to D,L-aminobutyric acid (Japanese Published Unexamined Patent Application No. 160592/88), a process using microorganisms having resistance to thiazole alanine and requirement for leucine, isoleucine or threonine (Japanese Patent Publication No. 116/77), and a process using microorganisms having resistance to aminoethylcysteine (Japanese Patent Publication No. 2678/83).

SUMMARY OF THE INVENTION

The present invention provides a process for, producing L-valine which comprises cultivating a microorganism which belongs to the genus Corynebacterium or Brevibacterium, which exhibits a) an ability to produce L-valine, b) resistance to L-valine in a medium containing acetic acid as a sole carbon source, and c) sensitivity to a pyruvic acid analog in a medium containing glucose as a sole carbon source, accumulating L-valine in the culture medium and recovering L-valine therefrom.

DETAILED DESCRIPTION OF THE INVENTION

The present invention will be described in detail hereinbelow.

Microorganisms of the present invention are Coryneform glutamic acid producing bacteria that belong to the genus Corynebacterium or Brevibacterium and exhibit a) an ability to produce L-valine, b) resistance to L-valine in a medium containing acetic acid as a sole carbon source, and c) sensitivity to a pyruvic acid analog in a medium containing glucose as a sole carbon source. Microorganisms having such characteristics are derived from glutamic acid producing Coryneform bacteria described below:

| | |
|---|---|
| Corynebacterium glutamicum | ATCC 13032 |
| Corynebacterium acetoacidophilum | ATCC 13870 |
| Corynebacterium herculis | ATCC 13868 |
| Corynebacterium lilium | ATCC 15990 |
| Brevibacterium flavum | ATCC 14067 |
| Brevibacterium lactofermentum | ATCC 13869 |
| Brevibacterium divaricatum | ATCC 14020 |
| Brevibacterium thiogenitalis | ATCC 19240 |

Growth of these strains in a medium containing acetic acid as a sole carbon source is inhibited by L-valine.

The microorganisms used in the present invention can be obtained by selecting mutants which do not exhibit sensitivity to L-valine in a medium containing acetic acid as a sole carbon source and L-valine at a concentration to which the parent strain is sensitive, and then selecting, from the resultant mutants, those which are sensitive to a pyruvic acid analog at a concentration to which the parent strain is not sensitive in a medium containing glucose as a sole carbon source. Alternatively, the microorganisms to be used in the present invention can also be obtained by selecting mutants which are sensitive to a pyruvic acid analog at a concentration to which the parent strain is not sensitive in a medium containing glucose as a sole carbon source, and then selecting, from these mutants, those which do not exhibit sensitivity to L-valine in a medium containing acetic acid as a sole carbon source and L-valine at a concentration to which the parent strain is sensitive.

The invention will be described concretely hereinbelow. First, a parental strain is mutagenized with a usual method such as irradiation with ultraviolet light or treatment with N-methyl-N'-nitro-N-nitrosoguanidine (referred to as "NTG", hereinafter) or with nitrous acid. Second, large colonies which have grown in a medium containing acetic acid as a sole carbon source and L-valine, or alternatively small colonies which have grown in a medium containing glucose as a sole carbon source and a pyruvic acid analog, are selected. Subsequently, mutants which also possess the remaining characteristics are selected. Examples of the pyruvic acid analog which can be used in the present invention include β-fluoropyruvic acid, β-bromopyruvic acid, β-chloropyruvic acid, β-cyclohexylpyruvic acid, β-mercaptopyruvic acid, β-imidazolylpyruvic acid, trimethylpyruvic acid, β-hydroxypyruvic acid, β-ketobutyric acid, etc.

The microorganisms of the present invention are characterized by showing resistance to L-valine in a culture medium containing acetic acid as a sole carbon source, and showing sensitivity to a pyruvic acid analog in a culture medium containing glucose as a sole carbon source. They may have, in addition to the above mentioned characteristics, other characteristics such as auxotrophy and resistance to amino acid analogs those of which are known to give the L-valine productivity to microorganisms. Strains carrying these multiple mutations can be obtained by successive mutagenesis, or by crossing the strains having different mutation via protoplast fusion.

The production of L-valine by a microorganisms according to the present invention can be achieved by a usual cultivation method. As a culture medium to be used, any synthetic medium or natural medium can be utilized, provided that it contains suitable amounts of a carbon source, a nitrogen source and an inorganic substance and trace amounts of nutrients which the selected strain requires.

As the carbon sources, carbohydrates such as glucose, glycerol, fructose, sucrose, maltose, mannose, starch, starch hydrolyzate, and molasses; polyalcohols; organic acids such as pyruvic acid, fumaric acid, lactic acid and acetic acid, can be used. Furthermore, hydrocarbons or alcohols can also be used as a carbon source, depending upon the assimilability of the microorganisms used.

As the nitrogen sources, ammonia; ammonium salts of inorganic and organic acids such as, ammonium chloride, ammonium sulfate, ammonium carbonate and ammonium acetate; urea; and other nitrogen-containing compounds, peptone, NZ-amine, meat extract, yeast extract, corn steep liquor, casein hydrolyzate, fish meal and digested substances thereof, can be used.

As the inorganic substances, potassium dihydrogenphosphate, dipotassium hydrogenphosphate, ammonium sulfate, ammonium chloride, magnesium sulfate, sodium chloride, ferrous sulfate, manganese sulfate, calcium carbonate and the like, can be used.

Cultivation is carried out under aerobic condition with shaking or aeration. In general, the temperature of the cultivation is in the range of from 20° to 40° C. preferred that the pH of the medium is maintained around neutrality during the culture. A cultivation period is usually in the range of from 1 to 5 days.

After the cultivation is completed, the recovery of L-valine from the culture broth is carried out according to a known method. For example, the cells are removed from the broth and the remaining supernatant is concentrated and crystallized after treating with active charcoal and/or ion exchange resin, etc.

The present invention will further be illustrated with reference to Examples.

EXAMPLE 1

*Corynebacterium glutamicum* ATCC 13032 was cultivated at 30° C. for 16 hours in a complete medium (prepared by dissolving 20 g of powdery bouillon and 5 g of yeast extract in 1 liter of water, pH adjusted to 7.2). Then the cells were collected and washed with 0.05M tris-maleic acid buffer (pH 6.0), and then suspended in the same buffer to a concentration of about 109 cells/ml. NTG was then added to a final concentration of 500 mg/l, and the mixture was maintained at 30° C. for 20 minutes. Thus treated cells were then washed with the same buffer and spread on an agar medium containing 0.5 g/l L-valine in a minimal medium of the composition as shown in Table 1.

TABLE 1

(Composition of Minimal Medium)

| | | |
|---|---|---|
| Sodium Acetate | 5 | g/l |
| $(NH_4)_2SO_4$ | 2 | g/l |
| $NH_4Cl$ | 3 | g/l |
| $KH_2PO_4$ | 1 | g/l |
| $K_2HPO_4$ | 3 | g/l |
| $FeSO_4.7H_2O$ | 10 | mg/l |
| $MnSO_4.4-6H_2O$ | 1 | mg/l |
| $(NH_4)_6Mo_7O_{24}.4H_2O$ | 0.04 | mg/l |
| Biotin | 30 | μg/l |
| Thiamine hydrochloride | 1 | mg/l |
| p-aminobenzoic acid | 5 | mg/l |
| Agar | 20 | g/l |
| | (pH 7.2) | |

After cultivation at 30° C. for 2 to 4 days, large colonies were picked up. Among these colonies, those were selected which grew slowly in the minimal medium containing 5 g/l glucose instead of sodium acetate in Table 1 as a carbon source and 6 mg/l β-fluoropyruvic acid (hereinafter, referred to as "βFP").

Thus, *Corynebacterium glutamicum* AV1 was selected as high L-valine producer, from these mutants.

*Corynebacterium glutamicum* AV1 was deposited with the Fermentation Research Institute of Agency of Industrial Science and Technology, Japan on Jul. 12, 1990 with the accession number of FERM BP-3006.

Table 2 shows the sensitivity of the parent strain ATCC 13032 and that of the mutant strain AV1 to L-valine and βFP. The sensitivity was evaluated as follows: In the case of the sensitivity to L-valine, a diluted cell suspension was spread on a minimal agar medium of the composition as shown in Table 1 containing 0.5 g/l L-valine, and in the case of the sensitivity to βFP, a diluted cell suspension was spread on a minimal agar medium containing 6 mg/l βFP and 5 g/l glucose as a carbon source. After incubation at 30° C. for 2 days, the sensitivity to L-valine or βFP was judged on the basis of colony size.

EXAMPLE 2

*Brevibacterium lactofermentum* ATCC 13869 was cultivated at 30° C. for 16 hours in a complete medium. Then, the cells were collected, washed with 0.05M tris-maleic acid buffer (pH 6.0), and suspended in the same buffer to a concentration of about 109 cells/ml. NTG was added to a final concentration of 500 mg/l, and the mixture was maintained at 30° C. for 20 minutes. Thus treated cells were then washed with the same buffer and spread on an agar medium of the composition as shown in Table 1 containing g/l L-valine.

After cultivation at 30° C. for 2 to 4 days, large colonies were picked up. Among them, those colonies were selected which grew slowly in the minimal medium containing 5 g/l glucose instead of sodium acetate as a carbon source and 6 mg/l βFP.

*Brevibacterium lactofermentum* AV11 was thus selected as high L-valine producer.

*Brevibacterium lactofermentum* AV11 was deposited with the Fermentation Research Institute of Agency of Industrial Science and Technology, Japan on Jul. 12, 1990 with the accession number FERM BP-3007.

Table 2 shows the sensitivity of the parent strain ATCC 13869 and the mutant strain AV11 to L-valine and to βFP. The sensitivity to L-valine and βFP was evaluated as in Example 1.

TABLE 2

| Carbon Source | L-Valine | βFP | ATCC 13032 | AV1 |
|---|---|---|---|---|
| Glucose | − | − | ++ | ++ |
| | − | + | ++ | + |
| Sodium Acetate | − | − | ++ | ++ |
| | + | − | + | ++ |

| Carbon Source | L-Valine | βFP | ATCC 13869 | AV11 |
|---|---|---|---|---|
| Glucose | − | − | ++ | ++ |
| | − | + | ++ | + |
| Sodium Acetate | − | − | ++ | ++ |
| | + | − | + | ++ |

+: Added  ++: large colonies
−: Not added  +: small colonies

EXAMPLE 3

*Corynebacterium glutamicum* AV1 (FERM BP-3006) and *Brevibacterium lactofermentum* AV11 (FERM BP-3007) obtained in Examples 1 and 2, as well as their parent strains were inoculated separately into a test tube containing 3 ml of seed medium (1% glucose, 2% powdery bouillon and 0.5% yeast extract; pH 7.2), and cultivated with shaking at 30° C. for 24 hours. Then, 1 ml of each resultant culture was inoculated into a 300-ml Erlenmeyer flask containing 20 ml of the fermentation medium having the following composition, and was cultivated with shaking at 30° C. for 48 hours. After cultivation, the filtrate of the culture broth was subjected to paper chromatography followed by color development with ninhydrin. The amount of the produced L-valine was measured colorimetrically.

The results are shown in Table 3. Composition of the fermentation medium used is as follows.

8% glucose, 0.1% $KH_2PO_4$, 0.1% magnesium sulfate, 5% ammonium sulfate, 0.2% urea, 120 µg/l thiamine hydrochloride, 180 µg/l biotin, 12 mg/l $FeSO_4 \cdot 7H_2O$, 12 mg/l $MnSO_4 \cdot 4$–$6H_2O$, 1% corn steep liquor, 2% calcium carbonate, pH=7.2.

TABLE 3

| Amount of L-valine Produced | |
|---|---|
| Strain | Amount of L-valine (mg/ml) |
| ATCC 13032 | 0.1 |
| AV1 | 3.9 |
| ATCC 13869 | 0.2 |
| AV11 | 3.6 |

What is claimed is:

1. A process for producing L-valine which comprises cultivating, in a medium, *Corynebacterium glutamicum* AV1 (FERM BP-3006) or *Brevibacterium lactofermentum* AV11 (FERM BP-3007), which exhibits a) an ability to produce L-valine, b) resistance to L-valine in a medium containing acetic acid as a sole carbon source, and c) sensitivity to a pyruvic acid analog in a medium containing glucose as a sole carbon source, until L-valine is accumulated in the culture broth, and recovering L-valine therefrom.

* * * * *